(12) United States Patent
Rucker et al.

(10) Patent No.: US 12,369,630 B2
(45) Date of Patent: Jul. 29, 2025

(54) VAPORISER WITH LID COMPRISING PROTRUSION

(71) Applicant: Simon Rucker, London (GB)

(72) Inventors: Simon Rucker, London (GB); Jeremy John Wright, London (GB); Alista Din Fe magrini, London (GB)

(73) Assignee: Simon Rucker, London (GB)

( * ) Notice: Subject to any disclaimer, the term of this patent is extended or adjusted under 35 U.S.C. 154(b) by 351 days.

(21) Appl. No.: 17/908,708

(22) PCT Filed: Mar. 2, 2021

(86) PCT No.: PCT/GB2021/050516
§ 371 (c)(1),
(2) Date: Sep. 1, 2022

(87) PCT Pub. No.: WO2021/176204
PCT Pub. Date: Sep. 10, 2021

(65) Prior Publication Data
US 2023/0132792 A1 May 4, 2023

(30) Foreign Application Priority Data
Mar. 3, 2020 (GB) ..................................... 2003018

(51) Int. Cl.
*A24F 40/42* (2020.01)
*A24F 40/20* (2020.01)

(52) U.S. Cl.
CPC .............. *A24F 40/42* (2020.01); *A24F 40/20* (2020.01)

(58) Field of Classification Search
CPC ................................. A24F 40/42; A24F 40/40
See application file for complete search history.

(56) References Cited

U.S. PATENT DOCUMENTS

| | | | |
|---|---|---|---|
| 8,669,349 | B2 | 3/2014 | Johnson et al. |
| 10,994,087 | B2 | 5/2021 | Rucker |
| 11,026,449 | B2 | 6/2021 | Mironov |
| 11,173,260 | B2 | 11/2021 | Golovanova et al. |
| 11,305,076 | B2 | 4/2022 | Emmett et al. |
| 11,364,354 | B2 | 6/2022 | Reevell |
| 2015/0343159 | A1 | 12/2015 | Farr et al. |
| 2019/0380391 | A1 | 12/2019 | Reevell |
| 2021/0112872 | A1 | 4/2021 | Rogan et al. |
| 2021/0386119 | A1 | 12/2021 | Plevnik et al. |

FOREIGN PATENT DOCUMENTS

| | | | | |
|---|---|---|---|---|
| EP | 3277112 B1 | * | 7/2019 | ............... A24C 5/01 |
| GB | 2534212 | | 7/2016 | |
| GB | 2534214 | | 7/2016 | |
| GB | 2553773 | | 3/2018 | |

(Continued)

*Primary Examiner* — Linda L Gray
(74) *Attorney, Agent, or Firm* — Levy & Grandinetti

(57) ABSTRACT

A vaporiser device (1) comprising a heating chamber (2) for receiving a sachet of herbal material (3) to be heated with which said vaporiser (1) is used, and a lid (4) which is movable between an open position in which an internal area (5) of said heating chamber (2) is accessible and a closed position in which said lid (4) overlies said internal area (5), and in which said lid (4) comprises a protrusion (6) on an underside (7) thereof which extends into said internal area (5) in said closed position.

13 Claims, 3 Drawing Sheets

(56) References Cited

FOREIGN PATENT DOCUMENTS

| WO | WO 2009/151717 | 12/2009 | | |
|----|----------------|---------|---|---|
| WO | WO 2014/006135 | 1/2014 | | |
| WO | WO 2016/162446 | 10/2016 | | |
| WO | WO-2016171997 A2 * | 10/2016 | ............ | A24F 42/60 |
| WO | WO 2017/102633 | 6/2017 | | |
| WO | WO 2017/202953 | 11/2017 | | |
| WO | WO 2017/202965 | 11/2017 | | |
| WO | WO 2018/146071 | 8/2018 | | |
| WO | WO 2019/224069 | 11/2019 | | |
| WO | WO 2020/104490 | 5/2020 | | |

* cited by examiner

VAPORISER WITH LID COMPRISING PROTRUSION

The present invention relates to a vaporiser for vaporising herbal materials, which has a lid comprising a protrusion.

Herbal vaporisers are electronic devices which heat a herbal material to a pre-determined temperature in a heating chamber in order to release an aerosol for consumption. The herbal material is not burnt, rather it is heated only sufficiently for the active ingredient to boil and be released as a consumable vapour. Such devices are distinct from electronic atomisers or e-cigarettes which heat a prepared liquid product to release an aerosol for consumption.

Herbal vaporisers are likely to be a less harmful way to consume a herbal product like tobacco or medical marijuana than smoking it, because the aerosol contains far less of the many carcinogenic, mutagenic and teratogenic bi-products created by combustion.

In comparison to atomisers and the like which can produce a consumable vapour at any time, herbal vaporisers are beneficial because they heat all the herbal material placed in them at once, meaning that users have to make a conscious decision to use them. This means users can more easily regulate or track their consumption.

However, known herbal vaporisers are designed to heat loose herbal material, which has to be ground to the correct particle size, and then has to be loaded manually into a heating chamber of the device before the consumption process is begun. The spent herbal material then has to be removed therefrom at the end. This approach appeals to some, who may enjoy the process. However, for others it is time consuming, and can be messy and fiddly. In particular, it may be considered a disadvantage in comparison to atomizers and the like, which consume easy to load cartridges of liquid. These are much easier to use on the go than herbal vaporisers. As such, some people may not adopt herbal vaporisers for these reasons.

In addition, when loose herbal material is placed into the heating chamber of a device, it may be arranged irregularly therein, in particular if the heating chamber is not fully filled with material. As such, the process of heating the loose material may not be optimal, as the conduction of heat from the surface of the heating chamber may not reach it all, or may not heat it all in a regular manner.

In order to address some of these problems GB2553773 in the name of the applicant disclosed a vaporiser with a removable container disposed in the heating chamber, the removable container comprising a vapour permeable membrane enclosing a herbal vapour producing material to be heated. The removable container is a consumable product with prepared herbal material inside it, which is placed in the vaporiser for consumption in a simplex action, and then removed therefrom after the herbal product has been heated, again in a simplex action. This removes from the end user the requirements to prepare the loose herbal material, to load the device manually with it, and then to empty and clean it at the end of the process.

However, GB2553773 only disclosed some basic designs of removable container, most of which are not practical from a low cost, high speed manufacturing perspective. One particular design of removable container disclosed was a tube of vapour permeable paper enclosing a herbal vapour producing material to be heated, and which was closed at both ends by one or more of a heat seal component, an adhesive component, an ultrasonic weld, a crimping component, a stitching component, a staple component or a punched material component. Such a container is similar to a teabag or snus sachet.

This sachet design is now preferred, but it does suffer from some drawbacks. Principal among these is its flat shape and flexible structure, which means that placing it in a known heating chamber requires it to be rolled or folded up for placement therein. This is not difficult, but it is not particularly sophisticated either. In addition, if the sachet is rolled or folded up this results in the paper being interspersed with the herbal material inside the heating chamber, which can result in less than optimal consumption characteristics.

The present invention is intended to address some of the above described problems.

Therefore, according to the present invention a vaporiser device comprises a heating chamber for receiving a sachet of herbal material to be heated with which said vaporiser is used, and a lid which is movable between an open position in which an internal area of said heating chamber is accessible and a closed position in which said lid overlies said internal area, and in which said lid comprises a protrusion on an underside thereof which extends into said internal area in said closed position.

Thus, in its most basic form the present invention involves the use of the protrusion on the underside of the lid to push the sachet of herbal material down into the heating chamber, pinning it against the surface thereof. This removes the requirement of the user to manipulate the sachet in any way prior to loading in the heating chamber, and it also serves to effectively apply one whole side of the sachet to the source of heat, thereby improving vaporisation performance.

The vaporiser device can comprise a mounting surface, and an opening can be formed in the mounting surface which can lead into the heating chamber. The underside of the lid can then comprise a portion which can overlie at least a portion of the mounting surface in the closed position. In use the mounting surface provides a platform on which the user can place the sachet of herbal material, prior to closure of the lid. It therefore rests above the heating chamber, before being pushed down therein by the protrusion as the lid moves to the closed position. One of the closed ends of the sachet which is left protruding from the heating chamber can then be held in place between the underside of the lid and the mounting surface.

The protrusion can take any physical form capable of extending into the heating chamber and pinning the sachet of herbal material therein. Likewise, the heating chamber can also take any physical form of concavity. However, in a preferred construction the heating chamber and the protrusion can comprise substantially corresponding physical shapes in a first plane, such that in the closed position a containment area is created inside the heating chamber which comprises a substantially regular depth from a first end to a second end thereof in the plane. This construction ensures that the sachet of herbal material is held against the surface of the heating chamber in the same manner across its length.

Preferably the heating chamber can be substantially U-shaped in the first plane, and can have the same U-shaped cross-sectional shape along a first axis normal to the first plane. The protrusion can then be substantially shaped in the first plane as a probe with a rounded end, and it can have the same probe-shaped cross-sectional shape along the first axis. In other words, the heating chamber is shaped like a rounded trough and the protrusion is shaped like a wall with a rounded end. This shape works well with a sachet of herbal material of the kind described above, which has a generally square-shaped pouch portion containing the herbal material, and generally rectangular closed ends.

In one version of the invention the heating chamber can have a cross-sectional shape along the first axis comprising a first wall, a rounded bottom and a second wall, and the second wall can be angled away from the first wall at a pre-determined angle. Preferably the second wall can be angled away from the first wall by substantially 15 degrees. The protrusion can then have a cross-sectional shape along the first axis comprising a first side, the rounded end and a second side, and the second side can be angled away from the first side by a pre-determined angle. Again, this can be substantially 15 degrees. The purpose of these shapes is to better facilitate the loading and retention of the sachet of herbal material in the heating chamber. In particular, and as set out in further detail below, the lid can be movable about an axis which is arranged adjacent to the first wall of the heating chamber, which means that the protrusion enters the heating chamber from that side. Having the second wall angled away from the first wall by substantially 15 degrees provides more space for the protrusion and the sachet of herbal material to move into and out of the heating chamber in use. If this construction were not used there would be a greater risk of jamming in use.

The mounting surface can comprise a first rectangular portion disposed adjacent to a top of the first wall and normal thereto, and a second rectangular portion adjacent to a top of the second wall and in line with the first rectangular portion. The underside of the lid can comprise a first part adjacent to a bottom of the first side of the protrusion and a second part adjacent to a bottom of the second side of the protrusion. A section of the second part of the underside of the lid can then overlie the second portion of the mounting surface in the closed position. With this construction the part of the sachet of material on the opposite side of the heating chamber to the axis of rotation of the lid is the part which is held between the underside of the lid and the mounting surface in the closed position. This helps to keep the sachet of herbal material in place in the closed position.

The first part of the underside, which is that closest to the axis of rotation of the lid, can comprise a concavity adapted to receive a first end of the sachet when the lid is in the open position. This feature allows for the sachet of herbal material to be optimally placed on the mounting surface, and over the heating chamber, prior to loading. In particular, the sachet of herbal material with which the vaporiser is intended to be used is of such a length that in order for a filled pouch portion thereof to be located in the correct position over the heating chamber a clearance gap is required beyond the first wall to accommodate its closed first end. The concavity provides such a clearance gap.

The vaporiser can comprise an elongate outer body extending along a second axis normal to the first axis. The mounting surface can then be provided at a first end of the outer body, and the outer body can comprise a rear side in a second plane normal to the mounting surface. The lid can be arranged relative to the outer body such that in the open position a base of the concavity is disposed on an opposite side of the second plane to the outer body. Therefore, the concavity and the arrangement of the lid provides a significant clearance gap for the sachet of herbal material in the open position. The clearance gap is eliminated as the lid moves from the open position to the closed position, but this occurs as the sachet of herbal material is pushed down into the heating chamber, leading to its first end travelling towards the heating chamber. The closed first end of the sachet of herbal material then protrudes from the heating chamber in the closed position, in a small area provided by the concavity, which in the closed position is located over the first portion of the mounting surface.

The lid can be connected to the outer body by a hinge, which can comprise a hinge axis which can be parallel to the first axis and can be located below the mounting surface. As discussed above, the hinge axis can be adjacent to the first wall of the heating chamber, which means it can be on the rear side of the outer body. Any known kind of hinge mechanism can be used for the hinge, including versions which can be manually dismantled so the lid can be removable from the outer body. For example, the outer body can comprise a plurality of extensions and the lid can comprise a corresponding plurality of sockets into which the extensions can be a snap-fit. Alternatively, the hinge mechanism can be of the kind which cannot be manually dismantled. For example, it can feature a pin which passes respectively through the lid and the outer body to connect them together. In addition, the hinge can be spring loaded in either rotational direction by a spring element, or it can be free to rotate without restriction. In the latter case the lid can comprise a pair of small spigots, and the outer body can comprise a pair of small slots into which the small spigots can be a snap-fit in order to retain the lid in the closed position, and prevent it from freely moving to the open position in use.

The lid can comprise a stop surface which can contact the rear side in the open positon, and delimit the movement of the lid beyond the open position. The stop surface can be angled relative to the rear side such that the lid can be arranged at substantially 15 degrees to the second plane in the open position. This configuration achieves a number of things. Firstly, it means that the lid opens up far enough for the protrusion not to occupy any space over the heating chamber, thereby allowing easy access. It also ensures that the clearance gap is of the correct size in the open position. As the same time, by delimiting the movement of the lid it ensures that the lid is arranged conveniently in the open position for a user to readily rotate it into the closed position. If holding the outer body in their palm they can easily flip the lid shut using a finger or their thumb.

In one version of the invention the outer body can comprise a first extension adjacent to a first edge of the mounting surface and a second extension adjacent to a second edge of the mounting surface. The lid can then comprise a lid body disposed between the first extension and the second extension in the closed position. A top side of the lid and outer ends of the first extension and the second extension can then collectively define an outer end surface of the outer body in the closed position, which outer end surface is normal to the second plane. With this construction the lid is protected on either side in the closed position. It also means that when the lid is in the closed position the vaporiser has a neat and ergonomic outer shape without any protruding shapes which the lid might otherwise generate.

A first air passageway can extend from an outer surface of the outer body into the heating chamber, and a second air passageway can extend from the heating chamber to a mouthpiece provided at a second end of the outer body. The first air passageway allows for air to be drawn over the sachet of herbal material as it is heated, and for the vapour to be generated in the known way. The second air passageway then allows for the vapour to be drawn from the heating chamber, and be directed to the user via the mouthpiece.

It will be appreciated that a vaporiser of the invention can be manufactured and supplied for use without any sachet of herbal material, which can then be provided separately. Such a stand-alone vaporiser falls within the scope of claim 1 below. However, one particular feature of the invention only emerges once a sachet of herbal material is placed in the heating chamber. Therefore, in one version of the invention the vaporiser can comprise such a sachet of herbal material to be heated removably disposed in the heating chamber. The sachet can comprise a tube of vapour permeable material enclosing a herbal vapour producing material to be heated, and which is closed at both ends by one or more of a heat seal component, an adhesive component, an ultrasonic weld, a crimping component, a stitching component, a staple component or a punched material component. The sachet can also comprise a laterally extending handle portion at a second end thereof. The vaporiser can comprise an outer body, and the laterally extending handle portion can protrude from a front side of the outer body.

The laterally extending handle portion can be formed by providing an extended length of closed section at the second end of the tube of vapour permeable material. In one version of the invention the laterally extending handle portion can further comprise a visual element. This can be printed thereon, or it can be formed in relief thereon. What this means is that in use a section of the sachet carrying a visual element such as a trade mark, logo, or other insignia can protrude from the front side of the body when a sachet is loaded therein. This serves to provide an indication that the vaporiser can be used, and it also provides marketing or other brand affiliation possibilities.

As described above the heating chamber and the protrusion can comprise substantially corresponding physical shapes in a first plane, such that in the closed position a containment area can be created inside the heating chamber which can comprise a substantially regular depth from a first end to a second end thereof in the plane. A pouch portion of the sachet can then be removably disposed in the containment area, and be pinned against a surface of the heating chamber by the protrusion.

The invention can be performed in various ways, but one embodiment will now be described by way of example, and with reference to the accompanying drawings, in which.

Figure 1:
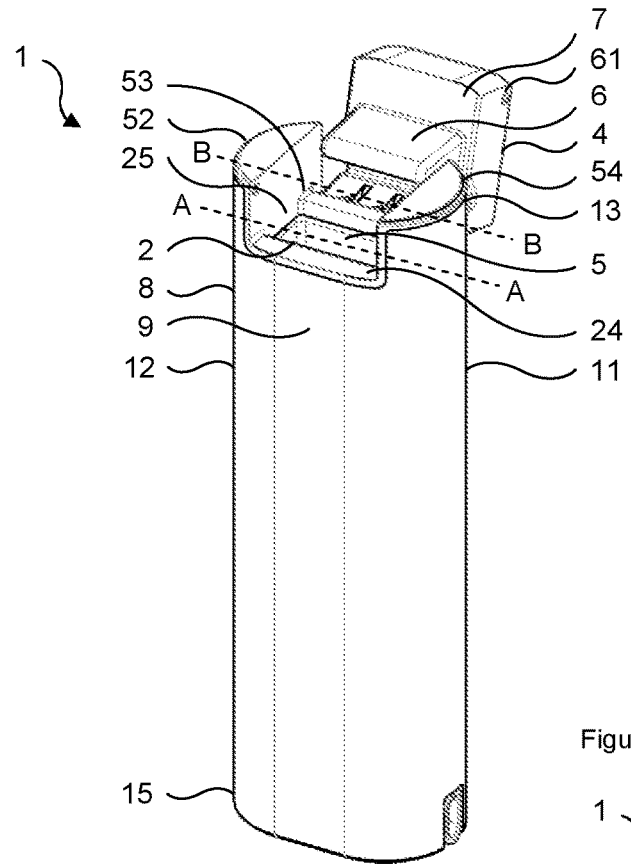
FIG. 1 is a perspective view of a vaporiser according to the present invention in an open position.
Figure 2:
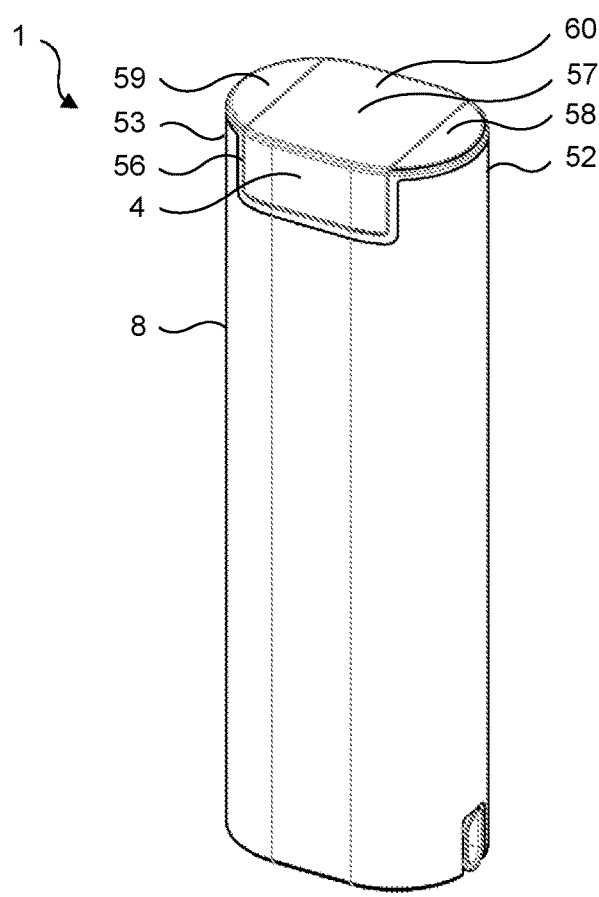
FIG. 2 is a perspective view of the vaporiser shown in FIG. 1 in a closed position.

As shown in FIG. 1 a vaporiser device 1 comprises a heating chamber 2 for receiving a sachet of herbal material 3 to be heated (shown in FIGS. 5 and 6), and a lid 4 which is movable between an open position, as shown in FIG. 1, in which an internal area 5 of the heating chamber 2 is accessible, and a closed position, as shown in FIG. 2, in which the lid 4 overlies the internal area 5, and in which the lid 4 comprises a protrusion 6 on an underside 7 thereof which extends into the internal area 5 in the closed position.

The vaporiser 1 is similar to known vaporiser devices in that it comprises an elongate outer body 8, within which is housed a heating mechanism (not visible) which supplies heat to the heating chamber 2, a rechargeable battery (not visible) which powers the heating mechanism, and electronic controls disposed on a PCB (not visible) which control the functioning of the vaporiser 1. The outer body 8 comprises a front side 9, a rear side 10, a left side 11 and a right side 12. As is clear from the Figures, the left side 11 and right side 12 are rounded, which produces a more ergonomic shape for the user to hold.

Figure 3:
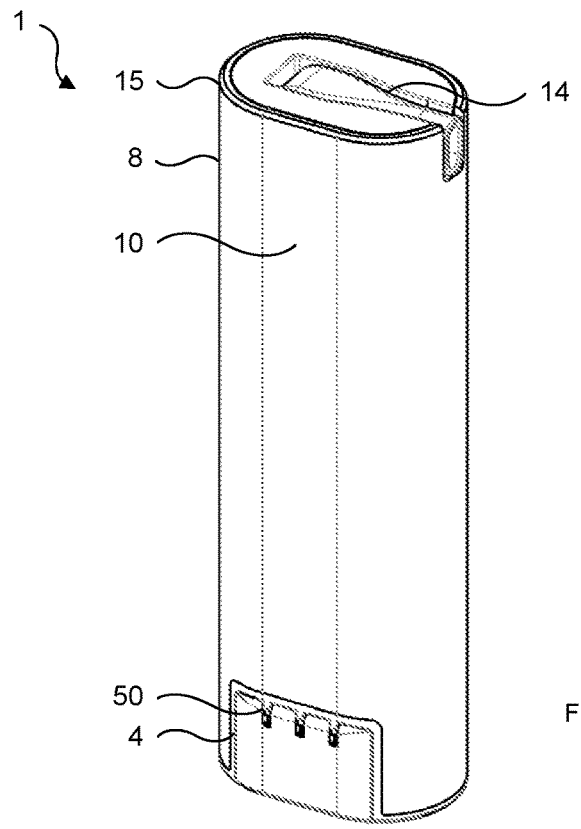
FIG. 3 is a perspective view of the vaporiser shown in FIG. 1 in a closed position.

The lid 4 is provided at a first end 13 of the outer body 8, and a mouth piece 14 is provided at a second end 15 of the outer body 8. Therefore, in use to consume vapour the vaporiser 1 would be oriented as shown in FIG. 3, with the second end 15 uppermost. The mouthpiece 14 can be moved from a stowed position as shown in FIG. 3, to an unfurled position (not shown) in which it is perpendicular to as shown in FIG. 3, and can be placed in the user's mouth. The vaporiser 1 also comprises control buttons 16, which are visible in FIG. 4, and which are arranged on the right side 12 of the outer body 8. The control buttons 16 are like those on known vaporisers and allow the user to operate the vaporiser 1 to produce vapour to be consumed, in the known way.

Figure 5:
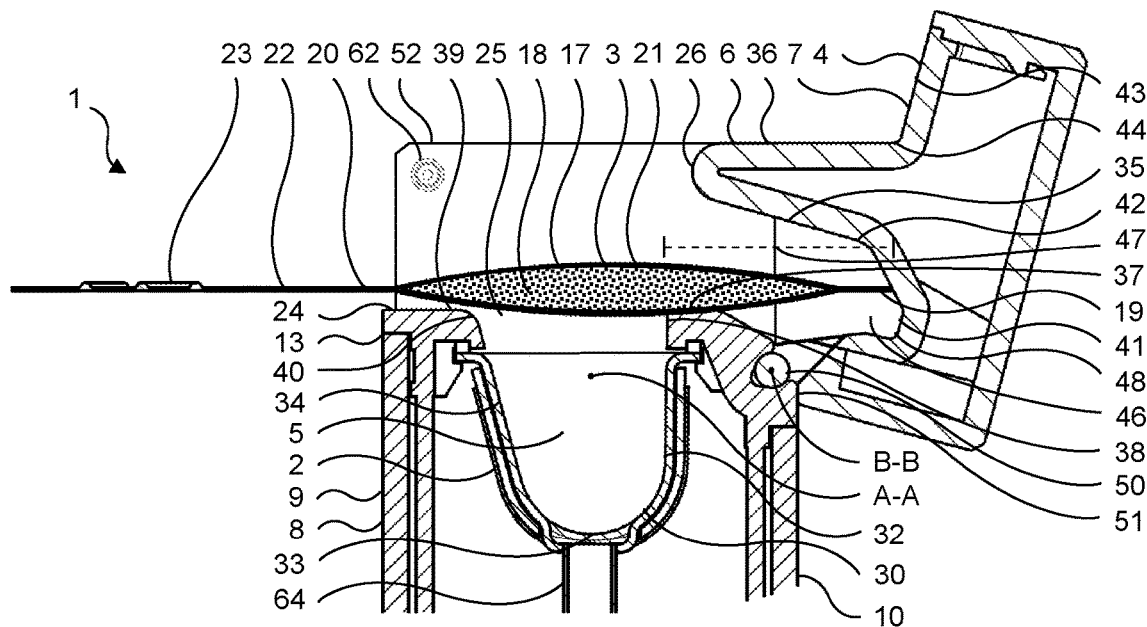
FIG. 5 is a partial cross-sectional side view of the vaporiser shown in FIG. 1 in an open position; and, FIG. 6 is a partial cross-sectional side view of the vaporiser shown in FIG. 1 in a closed position.
Figure 6:
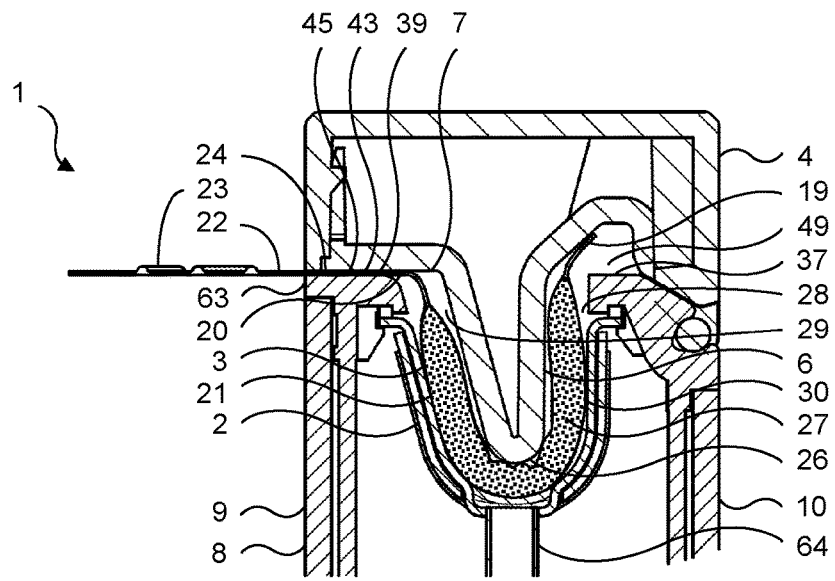

The vaporiser 1 can in theory be used with loose herbal material to be heated (not shown), or with any known kind of sachet of herbal material which would fit inside the heating chamber 2. However the vaporiser 1 is intended to be used with sachets of herbal material 3 of a particular construction, as shown in FIGS. 5 and 6. Namely, the sachet 3 comprises a tube of vapour permeable material 17 enclosing a herbal vapour producing material 18 to be heated, and which is closed at both a first end 19 and a second end 20 thereof by a heat seal component (not visible). This results in a central pouch portion 21 being formed. The sachet 3 also comprises a laterally extending handle portion 22 at the second end 20 thereof, which is formed by providing an extended length of closed section at the second end 20 of the tube of vapour permeable material 17. The laterally extending handle portion 22 comprises a logo element 23 thereon formed in relief, which is created using a pressing tool. The laterally extending handle portion 22 provides a convenient mechanism to handle the sachet 3, and as explained further below, it creates a particular visual effect when protruding from the vaporiser 1 in use.

Referring to FIG. 5, the vaporiser 1 comprises a mounting surface 24 at the first end 13, and an opening 25 is formed in the mounting surface 24 which leads into the heating chamber 2. The mounting surface 24 provides a platform on which the user can place the sachet of herbal material 3, prior to closure of the lid 4, as shown in FIG. 5. The sachet 3 rests above the heating chamber 2, before being pushed down therein by the protrusion 6 as the lid 4 moves to the closed position, as shown in FIG. 6.

As illustrated in FIG. 5, the heating chamber 2 is generally U-shaped in a first plane. The first plane is, or is parallel to, the plane of the cross-section shown. The heating chamber 2 has the same cross-sectional shape along a first axis A-A which is normal to the first plane. In other words the heating chamber 2 is shaped like a rounded trough.

The protrusion 6 comprises a substantially corresponding physical shape to the heating chamber 2 in the first plane. Namely, the protrusion 6 is shaped in the first plane as a probe with a rounded end 26, and it has the same probe-shaped cross-sectional shape along the first axis A-A. In other words, the protrusion 6 is shaped like a wall with a rounded end 26.

As a result of this, in the closed position a containment area 27 is created inside the heating chamber 2 which comprises a substantially regular depth from a first end 28 to a second end 29 thereof in the first plane. This construction ensures that the sachet of herbal material 3 is held against the surface 30 of the heating chamber 2 in generally the same manner across its length, as shown in FIG. 6. It is also held in the same way along its width along the first axis A-A. The shapes of the heating chamber 2 and protrusion 6 therefore work effectively with the sachet 3, as it has a generally square-shaped pouch portion 21 containing the herbal material 18, and the first end 19 and second end 20 are rectangular in shape.

The heating chamber 2 has a cross-sectional shape along the first axis A-A which is not quite U-shaped, because it comprises a first wall 32, a rounded bottom 33 and a second wall 34 which is angled away from the first wall 32 by 15 degrees. Likewise, the protrusion 6 has a cross-sectional shape along the first axis A-A comprising a first side 35, the rounded end 26 and a second side 36 which is angled away from the first side 35 by 15 degrees.

The purpose of these angular relationships between the first wall 32 and the second wall 34, and between the first side 35 and the second side 36, is to better facilitate the loading and retention of the sachet of herbal material 3 in the heating chamber 2. In particular, and as set out in further detail below, the lid 4 is movable about a hinge axis B-B which is arranged adjacent to the first wall 32 of the heating chamber 2, which means that the protrusion 6 enters the heating chamber 2 from that side. Having the second wall 34 angled away from the first wall 32 by 15 degrees provides more space for the protrusion 6 and the sachet of herbal material 3 to move into and out of the heating chamber 2 in use. In particular, the planetary path the rounded end 26 of the protrusion 6 takes about the hinge axis B-B when the lid 4 moves from the open position to the closed position takes it close to the second wall 34. If the second wall 34 were parallel to the first wall 32 there would be a greater risk of jamming the sachet 3 between the protrusion 6 and the first wall 32. Instead, with the construction shown, the sachet 3 passes smoothly into the heating chamber 2, to be held snugly therein as shown in FIG. 6.

Another way to consider these shapes is to appreciate that the containment area 27 needs to be generally the same volume as the pouch portion 21, so the pouch portion 21 is held snugly in place in the closed position. The sachet 3 contains a pre-determined amount of the herbal material 18, which therefore determines the required volume of the containment area 27. The heating chamber 2 and/or the protrusion 6 cannot be too large or too small respectively, or the invention will not function effectively. In particular, the protrusion 6 needs to be long enough to extend into the heating chamber 2 to a sufficient degree. In order to achieve this while also providing a hinged lid 4 within the confines of an ergonomically sized vaporiser 1, it is necessary to angle the second wall 34 at 15 degrees to the first wall 32, so as to provide the necessary clearance for the protrusion 6 to enter and leave the heating chamber 2.

Furthermore, by providing the heating chamber 2 with a slightly opened U-shape (by 15 degrees), less force is required to push the sachet 3 therein. It therefore contorts relatively easily as it is forced down into the resulting containment area 27. The sachet 3 can also be more readily removed from the heating chamber 2 thereafter.

Referring to the mounting surface 24 in greater detail, it comprises a first rectangular portion 37 disposed adjacent to a top 38 of the first wall 32 and normal thereto, and a second rectangular portion 39 adjacent to a top 40 of the second wall 34 and in line with the first rectangular portion 37. The first rectangular portion 37 and the second rectangular portion 39 provide support for the sachet of herbal material 3 when it is placed on the mounting surface 24 in a pre-loading position, as shown in FIG. 5.

Referring to the underside 7 of the lid 4 in greater detail, it comprises a first part 41 adjacent to a bottom 42 of the first side 35 of the protrusion 6, and a second part 43 adjacent to a bottom 44 of the second side 36 of the protrusion 6. The lid 4 is so configured that a forward section 45 of the second part 43 overlies the second portion 39 of the mounting surface 24 in the closed position, as shown in FIG. 6. As a result, the second end 20 of the sachet 3, and a part of the laterally extending handle portion 22, are held between the underside 7 of the lid 4 and the mounting surface 24 in the closed position. This helps to keep the sachet of herbal material 3 in place in the closed position, but it also results in the rest of the handle portion 22 protruding from the front side 9 of the outer body 8 of the vaporiser 1. It does so perpendicular to the front side 9, and such that the logo element 23 is visually presented on the handle portion 22 in an eye-catching way.

The first part 41 of the underside 7 comprises a concavity 46 which is adapted to receive the first end 19 of the sachet 3 when the lid 4 is in the open position, as shown in FIG. 5. In particular, the concavity 46 is so shaped that when the first end 19 of the sachet 3 is placed against it, the pouch portion 21 is optimally positioned over the heating chamber 2, prior to insertion therein. Or, looking at it another way, the sachet 3 is of such a length that in order for the pouch portion 21 to be located in the correct position over the heating chamber 2 a clearance gap 47 is required beyond the first wall 32 to accommodate its first end 19, and the concavity 46 provides such a clearance gap 47.

The clearance gap 47 is created as a result of the shape and configuration of the lid 4. In particular, the rear side 10 of the outer body 8 is in a second plane normal to the mounting surface 24, and as is clear from FIG. 5 the lid 4 is arranged relative to the outer body 8 such that in the open position a base 48 of the concavity 46 is disposed on an opposite side of the second plane to the outer body 8. As such, much of the clearance gap 47 is rearward of the rear side 10 of the outer body 8.

The clearance gap 47 is eliminated as the lid 4 moves from the open position to the closed position as shown in FIG. 6, but this occurs as the sachet 3 is pushed down into the heating chamber 2 by the protrusion 6, leading to its first end 19 travelling towards the hearing chamber 2. The first end 19 then protrudes from the heating chamber 2 in the closed position, and is accommodated in a small area 49 provided by the concavity 46, which in the closed position is located over the first portion 37 of the mounting surface 24.

The lid 4 is connected to the outer body 8 by a hinge 50 on the rear side 10. The hinge 50 defines the hinge axis B-B which is parallel to the first axis A-A, and which is located below the mounting surface 24. The outer body 8 comprises three extensions 50a and the lid 4 comprises three corresponding sockets 50b in which the extensions 50a are located to facilitate the hinge 50. A pin (not visible) passes respectively through the sockets 50b and the extensions 50a to fix the lid 4 to the outer body 8, so it cannot be removed. The lid 4 is free to rotate on the hinge 50 without restriction between the open and closed positions.

As discussed above, the hinge axis B-B defines the planetary path of the end 26 of the protrusion 6 as the lid 4 moves between the open and closed positions. That planetary path of the end 26 of the protrusion 6 is downward as the lid 4 moves from the open position to the closed position, because the end 26 of the protrusion 6 is forward of the hinge axis B-B. The hinge axis B-B also defines the planetary path of the concavity 46 as the lid 4 moves between the open and closed positions. The planetary path of the concavity 46 is initially upward before being downward as the lid 4 moves from the open position to the closed position, because the concavity 46 is rearward of the hinge axis B-B in the open position, and forward thereof in the closed position. Due to the shape of the concavity 46, and in particular that the base 48 thereof is rearward and below the first end 19 of the sachet 3 in the pre-loading position shown in FIG. 5, this means is that it does not exert any influence on the first end 19 of the sachet 3 until, or at approximately the same time as, the end 26 of the protrusion 6 begins to exert any influence on the pouch portion 21 of the sachet 3. Therefore, the shape of the concavity 46 and the position of the hinge axis B-B are designed to accommodate the shape of the sachet 31 in use, while still allowing the vaporiser 1 to be a compact and convenient size.

The lid 4 comprises a stop surface 51 which contacts the rear side 10 in the open positon, and delimits the movement of the lid 4 beyond the open position. The stop surface 51 is angled relative to the rear side 10 such that the lid 4 is arranged at substantially 15 degrees to the second plane in the open position, as is clear from FIG. 5. The angle of the stop surface 51 achieves a number of things. Firstly, it means that the lid 4 opens up far enough for the protrusion 6 not to occupy any space over the heating chamber 2 in the open position, thereby allowing easy access. This is particularly relevant when the sachet 3 is to be removed from the heating chamber 2 in use. It also ensures that the clearance gap 47 is of the correct size and orientation in the open position, as outlined above. As the same time, by delimiting the movement of the lid 4 the stop surface 51 ensures that the lid 4 is arranged conveniently in the open position for a user to readily rotate it into the closed position. If holding the outer body 8 in their palm they can easily flip the lid 4 shut using a finger or their thumb. Finally, with this angle of stop surface 51 the second side 36 of the protrusion 6 is normal to the second plane when the lid 4 is in the open position.

Referring back to FIGS. 1 and 2, the outer body 8 comprises a first extension 52 adjacent to a first edge 53 of the mounting surface 24 and a second extension 54 adjacent to a second edge (not visible) of the mounting surface 24. The lid 4 comprises a lid body 56 which is disposed between the first extension 52 and the second extension 54 in the closed position. The first extension 52, second extension 54 and the lid body 56 are so sized that a top side 57 of the lid 4 and outer ends 58 and 59 of the first extension 52 and the second extension 54 respectively combine to collectively define an outer end surface 60 at the first end 13 of the outer body 8 in the closed position, which outer end surface 60 is normal to the second plane. With this construction the lid 4 is protected on either side in the closed position by the first extension 52 and the second extension 54. It also means that when the lid 4 is in the closed position the vaporiser 1 has a neat and ergonomic outer shape without any protruding shapes which the lid 4 might otherwise generate.

The lid body 56 comprises a pair of small spigots on either side, one of which 61 is visible in FIG. 1, and the first extension 52 and the second extension 54 each comprise a pair of small slots 62 on their inward facing surfaces. The spigots 61 are a snap-fit into the slots 62 to releasably retain the lid 4 in the closed position.

A first air passageway extends from an outer surface 63 of the outer body 8 into the heating chamber 2. The first air passageway is not visible as such in the Figures because it takes the form of the any gap or gaps between the lid 4 and the outer body 8 when the lid 4 is in the closed position. Such a gap or gaps are present because the lid 4 is not sealed shut in the closed position, and sufficient clearance is present for air to pass freely into the heating chamber 2.

A second air passageway 64 extends from the heating chamber 2 to the mouthpiece 14. The first air passageway allows for air to be drawn over the sachet 3 as it is heated, and for the vapour to be generated in the known way. The second air passageway 64 then allows for the vapour to be drawn from the heating chamber 2, and be directed to the user via the mouthpiece 14.

In use the vaporiser 1 operates as follows. Firstly, the vaporiser 1 is provided with a source of electricity to charge the battery (not shown), in the know way. Once the battery is sufficiently charged to operate the vaporiser 1, the user can load a sachet 3 to consume. The user manually moves the lid 4 into the open position about the hinge 50, and they place the sachet 3 on the mounting surface 24 in the pre-loading position as shown in FIG. 5. In this position the pouch portion 21 is optimally located over the opening 25 in the mounting surface 24 which leads to the heating chamber 2, and the first end 19 of the sachet 3 is located in the concavity 46. The user can use the handle portion 22 of the sachet 3 to place it in this positon.

The user then manually moves the lid 4 about the hinge 50 into the closed position shown in FIG. 6. When the lid 4 reaches the closed position the spigots 61 enter the slots 62 and maintain the lid 4 in the closed position. As described above the hinge axis B-B defines the planetary path of the end 26 of the protrusion 6 as the lid 4 moves, and the end 26 travels in a downward direction because it is forward of the hinge axis B-B. As also described above, the second wall 34 of the heating chamber 2 is angled away from the first wall 32 by 15 degrees to provide sufficient clearance for the end 26 of the protrusion 6 to travel down into the heating chamber 2 with the pouch portion 21 of the sachet 3 wrapped around it.

As a result of the movement of the lid 4 the end 26 of the protrusion 6 comes into contact with the pouch portion 21 of the sachet 3, and pushes the pouch portion 21 down into the heating chamber 2, until it is disposed in the containment area 27 in the manner shown in FIG. 6. In particular, it generally extends from the first end 28 to the second end 29 thereof. This occurs because of the specific location of the pouch portion 21 in the pre-loading position, which can be determined by the user placing the first end 19 of the sachet 3 in the concavity 46 as shown in FIG. 5. If the sachet 3 were no so positioned then it may be pushed into the containment area 27 irregularly, and might not extend from the first end 28 to the second end 29 thereof. In the correct arrangement shown in FIG. 6 the pouch portion 21 of the sachet 3 is held in place against the surface 30 of the hearting chamber 2, by virtue of the lid 4 being retained in the closed position. This ensures that the maximum amount of heat from the surface 30 of the heating chamber 2 is transmitted to the herbal material 18 inside the pouch portion 21, which ensures high performance. The fact that the containment area 27 is relatively shallow in depth from its first end 28 to its second end 29 also means that all the herbal material 18 is located close to the surface 30 of the heating chamber 2, so it is all readily heated, which also ensures a high performance. It also means that when heat is applied, the herbal material 18 inside the pouch portion 21 is consumed in a regular fashion as it is all subjected to the same transmission of heat from the first end 19 to the second end 20 of the sachet 3.

In the closed position the concavity 46 provides the small area 49 over the first rectangular portion 37 of the mounting surface 24, and as is clear from FIG. 6 the first end 19 of the sachet 3 protrudes from the heating chamber 2 and is accommodated in the small area 49.

Furthermore, in the closed position the forward section 45 of the second part 43 of the underside 7 of the lid 4 overlies the second portion 39 of the mounting surface 24. As a result, the second end 20 of the sachet 3, and a part of the laterally extending handle portion 22, are held therebetween. This helps to keep the sachet 3 in place in the closed position, but it also results in the rest of the handle portion 22 protruding from the front side 9 of the outer body 8. It does so perpendicular to the front side 9, and such that the logo element 23 is visually presented on the handle portion 22 in an eye-catching way. This serves to provide an indication that the vaporiser 1 can be used as it is loaded, and it also provides brand affiliation.

Figure 4:
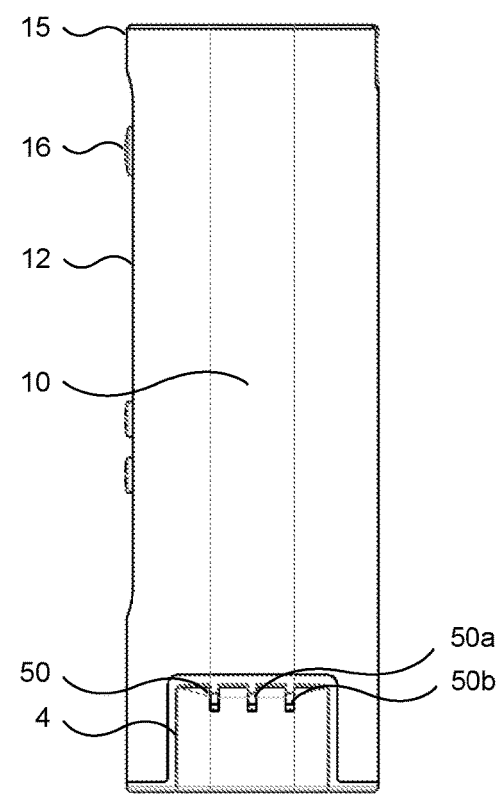
FIG. 4 is a side view of the vaporiser show in FIG. 1 in a closed position.

The vaporiser 1 is now ready to perform its vaporising function. The user turns the vaporiser 1 back to the upright position as shown in FIGS. 3 and 4, and manually moves the mouthpiece 14 from the stowed position as shown in FIG. 3, to an unfurled position (not shown) in which it is perpendicular to as shown in FIG. 3, and can be placed in the user's mouth. The user operates the control buttons 16 to activate the heating mechanism (not visible), which then supplies heat to the heating chamber 2, and the surface 30 in particular. The manner in which this is done is controlled by the PCB (not visible). As this is all known technology it is not further described here. This heat is then transmitted to the herbal material 18 inside the sachet 3 such that it is heated to a pre-determined temperature and releases an aerosol for consumption.

The user draws on the mouthpiece 14 which sucks air into the heating chamber 2 via the first air passageway. This air then collects with the generated aerosol vapour, before being sucked into the second air passageway 62, and consumed by the user via the mouthpiece 14. The user continues to use the vaporiser 1 in this way until the herbal material 18 no longer provides any further consumable aerosol vapour.

Once the sachet 3 is consumed in this way it can be removed from the vaporiser 1. The user manually moves the lid 4 back into the open position, which they do by exerting sufficient manual pressure to the lid body 56 to release the spigots 61 from the slots 62. The heating chamber 2 is then exposed and the sachet 3 can then be manually removed therefrom, which is most conveniently done by manipulating the lateral handle portion 22, before being disposed of. The vaporiser 1 is then ready to be used with another sachet of herbal material.

The vaporiser 1 can be altered without departing from the scope of claim 1. In particular, in one alternative embodiment (not shown) the protrusion is rod-shaped as opposed to being wall-shaped, and the heating chamber has a corresponding well shape as opposed to a trough shape.

In another alternative embodiment (not shown) the hinge can be manually dismantled to remove the lid from the outer body. The outer body comprises a plurality of extensions and the lid comprises a corresponding plurality of sockets into which the extensions are a snap-fit.

In other alternative embodiments (not shown) the hinge is spring loaded. In one version the hinge is spring loaded by a spring element acting thereon into the open position. This allows the lid to be more readily moved to the open position, and maintains the lid in that position. In another version the hinge is spring loaded by a spring element acting thereon into the closed position. This allows the lid to be more readily moved into the closed position, and helps to maintain the lid in that position.

In other alternative embodiments (not shown) the second wall is angled away from the first wall by angles other than 15 degrees, for example any angle between 10 and 20 degrees. This may be preferential in some cases in order to accommodate different sizes of parts or of sachets.

In another alternative embodiment (not shown) the mounting surface is provided with one or more grooves formed in its surface in order to increase the area of the first air passageway into the heating chamber. As explained above, the first air passageway takes the form of the any gap or gaps between the lid and the outer body when the lid is in the closed position. Such a gap or gaps are present because the lid is not sealed shut in the closed position, and sufficient clearance is present for air to pass into the heating chamber. The one or more grooves in the mounting surface effectively form a part of the first air passageway, and are implemented as required to improve or better regulate the flow of air into the heating chamber around the first end and second end of the sachet which are disposed on the mounting chamber. In another alternative embodiment (not shown) the underside of the lid is provided with one or more grooves formed in its surface in order to increase the area of the first air passageway into the heating chamber. These work in the same manner as described above. In another alternative embodiment both the mounting surface and the underside of the lid are provided with one or more grooves like those described above.

In another alternative embodiment (not shown) the sachet of herbal material is not provided with any lateral handle portion and its second end is the same as its first end.

Therefore, the present invention involves the use of the protrusion on the underside of the lid to push the sachet of herbal material down into the heating chamber, pinning it against the surface thereof. This removes the requirement of the user to manipulate the sachet in any way prior to loading in the heating chamber, and it also serves to effectively apply one whole side of the sachet to the source of heat, thereby improving vaporisation performance. Furthermore, the lateral handle portion of the sachet protrudes from the outer body when the sachet is loaded in the vaporiser, which provides a unique visual indication of the presence of the sachet, as well as a marketing and branding opportunity.

The invention claimed is:

1. A vaporiser device comprising a heating chamber for receiving a sachet of herbal material to be heated with which said vaporiser device is used, and a lid which is movable between an open position in which an internal area of said heating chamber is accessible and a closed position in which said lid overlies said internal area, in which said vaporiser device comprises a mounting surface for supporting a sachet in a pre-loading position and an opening formed in said mounting surface leading to said heating chamber, and in which said lid comprises a protrusion on an underside thereof which extends into said internal area in said closed position, said protrusion being configured to push the sachet down from said pre-loading position into said heating chamber when said lid is moved from said open position to said closed position.

2. A vaporiser device as claimed in claim 1 in which said heating chamber and said protrusion comprise substantially corresponding physical shapes in a first plane, such that in said closed position a containment area is created inside said heating chamber which comprises a substantially regular depth from a first end to a second end thereof in said plane.

3. A vaporiser device as claimed in claim 2 in which said heating chamber is substantially U-shaped in said first plane, and has the same U-shaped cross-sectional shape along a first axis normal to said first plane, and in which said protrusion is substantially shaped in said first plane as a probe with a rounded end, and has the same probe-shaped cross-sectional shape along said first axis.

4. A vaporiser device as claimed in claim 3 in which said heating chamber has a cross-sectional shape along said first axis comprising a first wall, a rounded bottom and a second wall, in which said second wall is angled away from said first wall by substantially 15 degrees, in which said protrusion has a cross-sectional shape along said first axis comprising a first side, said rounded end and a second side, and in which said second side is angled away from said first side by substantially 15 degrees.

5. A vaporiser device as claimed in claim 4 in which said mounting surface comprises a first rectangular portion disposed adjacent to a top of said first wall and normal thereto, and a second rectangular portion adjacent to a top of said second wall and in line with said first rectangular portion, in which said underside of said lid comprises a first part adjacent to a bottom of said first side of said protrusion and a second part adjacent to a bottom of said second side of said protrusion, and in which a section of said second part overlies said second portion in said closed position.

6. A vaporiser device as claimed in claim 5 in which said first part of said underside comprises a concavity adapted to receive a first end of said sachet with which said vaporiser device is used, when said lid is in said open position.

7. A vaporiser device as claimed in claim 6 in which said vaporiser device comprises an elongate outer body extending along a second axis normal to said first axis, in which said mounting surface is provided at a first end of said outer body, in which said outer body comprises a rear side in a second plane normal to said mounting surface, and in which said lid is arranged relative to said outer body such that in said open position a base of said concavity is disposed on an opposite side of said second plane to said outer body.

8. A vaporiser device as claimed in claim 7 in which said lid is connected to said outer body by a hinge, in which said hinge comprises a hinge axis parallel to said first axis, in which said hinge axis is located below said mounting surface.

9. A vaporiser device as claimed in claim 8 in which said lid comprises a stop surface which contacts said rear side in said open position and delimits movement of said lid beyond said open position, and in which said stop surface is angled relative to the rear side such that said lid is arranged at substantially 15 degrees to said second plane in said open position.

10. A vaporiser device as claimed in claim 9 in which said outer body comprises a first extension adjacent to a first edge of said mounting surface and a second extension adjacent to a second edge of said mounting surface, in which said lid comprises a lid body disposed between said first extension and said second extension in said closed position, in which a top side of said lid and outer ends of said first extension and said second extension collectively define an outer end surface of said outer body in said closed position, which outer end surface is normal to said second plane.

11. A vaporiser device as claimed in claim 10 in which a first air passageway extends from an outer surface of said outer body into said heating chamber, and a second air passageway extends from said heating chamber to a mouthpiece provided at a second end of said outer body.

12. A vaporiser device comprising a heating chamber and a lid which is movable between an open position in which an internal area of said heating chamber is accessible and a closed position in which said lid overlies said internal area, in which said lid comprises a protrusion on an underside thereof which extends into said internal area in said closed position, in which said vaporiser device comprises a sachet of herbal material to be heated removably disposed in said heating chamber, in which said sachet comprises a tube of vapour permeable material enclosing a herbal vapour producing material to be heated and which is closed at both ends by one or more of a heat seal component, an adhesive component, an ultrasonic weld, a crimping component, a stitching component, a staple component or a punched material component, in which said sachet comprises a laterally extending handle portion at an end thereof, in which said vaporiser comprises an outer body and in which said laterally extending handle portion protrudes from a front side of said outer body.

13. A vaporiser device as claimed in claim 12 in which said heating chamber and said protrusion comprise substantially corresponding physical shapes in a first plane, such that in said closed position a containment area is created inside said heating chamber which comprises a substantially regular depth from a first end to a second end thereof in said plane, and in which a pouch portion of said sachet is removably disposed in said containment area, and is pinned against a surface of said heating chamber by said protrusion.

* * * * *